United States Patent
Servello et al.

(10) Patent No.: US 8,121,305 B2
(45) Date of Patent: Feb. 21, 2012

(54) FETAL COMMUNICATION SYSTEM

(76) Inventors: Jennifer Servello, Yorktown Heights, NY (US); Sean Montecello, Myrtle Beach, SC (US); Lee Weinstein, Arlington, MA (US)

( * ) Notice: Subject to any disclaimer, the term of this patent is extended or adjusted under 35 U.S.C. 154(b) by 1073 days.

(21) Appl. No.: 12/004,624

(22) Filed: Dec. 22, 2007

(65) Prior Publication Data

US 2009/0161892 A1   Jun. 25, 2009

(51) Int. Cl.
*H04J 3/02* (2006.01)
(52) U.S. Cl. ......................................... 381/77
(58) Field of Classification Search .................. 381/77
See application file for complete search history.

(56) References Cited

U.S. PATENT DOCUMENTS

| | | | |
|---|---|---|---|
| 4,768,612 A | | 9/1988 | Hodson |
| 4,781,200 A | * | 11/1988 | Baker ........................ 600/483 |
| 4,798,539 A | | 1/1989 | Henry et al. |
| 4,830,007 A | | 5/1989 | Stein |
| 4,898,179 A | | 2/1990 | Sirota |
| 4,934,998 A | | 6/1990 | Thomas, Jr. |
| 5,033,968 A | | 7/1991 | Hecht |
| 5,109,421 A | | 4/1992 | Fox |
| 5,491,756 A | | 2/1996 | Francais |
| 5,596,647 A | * | 1/1997 | Wakai et al. .................. 381/77 |
| 5,699,558 A | | 12/1997 | Min |
| 5,764,776 A | | 6/1998 | Francais |
| D397,838 S | | 9/1998 | Waggoner et al. |
| 5,827,173 A | | 10/1998 | Lindsay |
| D407,623 S | | 4/1999 | Romo et al. |
| 5,898,787 A | | 4/1999 | Stanford |
| 5,913,834 A | | 6/1999 | Francais |

(Continued)

FOREIGN PATENT DOCUMENTS

AU 678182 B2 5/1997

(Continued)

OTHER PUBLICATIONS http://www.bpmlegal.com/wmomwlk.html Fetal Speaker System and Support Belt for Maternal Wear A fetal speaker system and support belt of the present invention includes a belt-like housing, a pair of low-volume speakers mounted spaced apart, and a casing with a resilient padding material therein. The belt fastens about the abdomen and adjusts accordingly to the growing belly. A radio or other audio transmitting device is maintained in position by a sturdy sleeve on the side of the belt . . .

(Continued)

*Primary Examiner* — Thao P. Le
(74) *Attorney, Agent, or Firm* — Russ Weinzimmer; Russ Weinzimmer & Associates PC (57) ABSTRACT

A compact fetal sound system delivers high-fidelity sound to a fetus in utero through a miniature, abdominally mounted driver with a convex diaphragm. No gel is necessary at the interface between the diaphragm and the mother's abdomen. Digital signal processing shapes the frequency spectrum of the sound transmitted to the fetus, so that after traveling through the attenuative tissue of the expectant mother the desired volume of sound and frequency content reach the ears of the fetus. As the term of pregnancy progresses, the frequency shaping provided by the digital signal processing automatically varies to compensate for changes in uterine lining thickness and the like. Preferred embodiments also include a microphone attached to the abdomen of the mother and signal processing to correct for frequency and amplitude distortions of sound eminating from the womb. Embodiments also include an elastic belt to maintain the transducer and microphone against the abdomen.

21 Claims, 11 Drawing Sheets

U.S. PATENT DOCUMENTS

| | | | |
|---|---|---|---|
| 6,097,822 | A | 8/2000 | Min |
| 6,169,814 | B1 | 1/2001 | Johnson |
| 6,718,044 | B1 | 4/2004 | Alleyne |
| 6,840,775 | B2 | 1/2005 | Sailors |
| 6,949,074 | B2 | 9/2005 | Fatemi |
| D529,896 | S | 10/2006 | Anderson et al. |
| 7,697,891 | B2 * | 4/2010 | Desrosiers et al. ............ 455/39 |
| 2003/0171937 | A1 * | 9/2003 | Fukumoto .................... 704/503 |
| 2006/0104451 | A1 * | 5/2006 | Browning et al. ............. 381/59 |
| 2009/0068964 | A1 * | 3/2009 | Gregg et al. .................... 455/91 |

FOREIGN PATENT DOCUMENTS

| | | |
|---|---|---|
| CA | 2114076 AA | 5/1995 |
| CN | 86105353 A | 4/1987 |
| GR | 1005003 B1 | 9/2005 |
| JP | 7255098 A2 | 3/1995 |
| JP | 11205878 A2 | 7/1999 |

OTHER PUBLICATIONS http://www.amazon.com/Baby-Plus-Prenatal-Education-System/dp/B0009EFYJE—Baby Plus Prenatal Education System—•Introduces a new level of neurological response, developing a stronger mental architecture •Audio lessons allow baby to discriminate the simple rhythmic sounds of BabyPlus from those of the month.

http://www.babybeebright.com/home.aspx With the Baby Bee Bright quality prenatal learning system, you can bond with your unborn baby while teaching early language skills and enhancing your baby's development.

http://cgi.ebay.co.uk/PRENATAL-LISTENING-SYSTEM_W0QQitemZ320057527264QQihZ011QQcategoryZ87170QQrdZ1QQ-cmdZViewItem?hash=item320057527264 Hear babys heartbeat, hiccups & kicks. 2 x headphones included . . . Recording cable included and CD guide.

* cited by examiner

FETAL COMMUNICATION SYSTEM

FIELD OF THE INVENTION

The invention relates generally to sound reproduction and transmission of sound into the human body, and more specifically to systems for transmitting audible sound to a fetus in utero.

BACKGROUND OF THE INVENTION

Recent research has indicated that a fetus responds to audible stimulation and that the effect of such audible stimulation may constitute an early teaching experience and may also have an impact on behavior and learning capability of the child after birth. In addition, the sounds of the mother's voice are thought to have a salutary effect upon a fetus.

More specifically, it has been shown that a fetus hears sounds as early as the fifth month of pregnancy. The experience a fetus has in hearing sounds, including the father's and mother's voices, may aid in early language development and bonding between parents and the child.

Studies have been conducted on both the ability of the fetus to hear noises and the ability of sounds to reach the fetus from outside the mother's body. One such study was discussed in "Perception auditive et reactivite foetale aux stimulations sonores," by D. Querleu et al., J. Gyn. Obst. Biol. Repr., 1981, Vol. 10, pp. 307-314 ("Auditory Perception and Reaction to Sonor Stimulation"). The authors of this article investigated the level of sound within the uterus, both internal background noise as well as external noise passing through the body. The article indicates that the global intensity of background noise within the uterus is about 65 decibels. Furthermore, it was found that sound sourced outside the mother is increasingly attenuated in the uterus as the frequency increases, at the rate of six to twelve decibels per octave, and that for sounds above 2000 hertz a dangerously loud sound would be required outside the mother to overcome background levels within the body. Finally, for a sound source of 110 decibels, the attenuation of the signal at 1,000 hertz is about 20 decibels.

A mother's voice or the voice of another person can be delivered much more effectively to a fetus through transducers positioned near the mother's abdomen, as compared to voices transmitted through the air or from the mother's larynx through the mother's body to the fetus.

The transmission of the sound of voices or music to a fetus through the mother's abdomen can have the effect of calming an otherwise overly active fetus. Additionally, studies have shown that babies, while listening to recordings of sounds from the womb, calmed down faster than when the recordings were not played. In the same way, audible recordings intentionally played to a fetus before it is born can be used after birth to soothe, educate, and entertain the baby.

To help parents use sound to benefit their gestating children, many systems have been developed that place sound generating devices adjacent to an expectant mother's abdomen and transmit sound through the womb to the fetus. Typically, these systems are designed to transmit voices of the parents, music originating from a recording or a radio, and/or other types of sounds such as heartbeats. Some include a method for moderating the sound level. Some help parents, doctors, or others monitor the effects of the stimulation on the fetus, for example through a stethoscope or like device. Typically, the devices are imbedded within a belt or vest like garment. A variety of materials have been used in this art, and some designs give attention to comfort and fashion as well as function.

In U.S. Pat. No. 4,830,007, Stein suggests that more efficient sound transmission to the fetus may be achieved by using sound transducers that are held in relatively close and solid contact with the abdominal area of the mother, so as to conduct the auditory vibrations directly into the skin of the abdomin, rather than allowing the sound to pass through the air before reaching the abdomin. This approach avoids significant attenuation of the sound as it passes through the air and across the air/abdomin interface, and also provides for efficient transmission of sound to the fetus while greatly reducing the amount of sound that is audible to the mother or to other persons in the vicinity. Such contact and transmission may be further enhanced by the use of a gel, which is applied either on the abdomen or on the transducer face prior to placement against the abdomen. The gel may be derived from a solution of gelatin or other thickening agent in water. It is suggested that sound transducers used for this purpose can be commercially available speakers, provided that the vibrating portion of the speaker is positioned substantially in firm contact with the external surface of the abdomen of the wearer.

The diaphragms of commercial loudspeakers are often quite delicate, being designed only to contact air, and not solid objects. Accordingly, there is a need for an acoustic transducer better suited for direct contact with an expectant mother's abdomen.

Some persons may have allergic reactions to gelatin in prolonged skin contact, and it can be inconvenient and messy to apply a gel to a transducer which is to be worn in contact with the skin. Accordingly, there is a need for an audio transducer which is designed for direct acoustic contact with skin, which does not require gel to make good acoustic contact.

While many sound-transmitting devices exist for pregnant women to use, there is a need for an improved apparatus that is more comfortable for expectant mothers and that more effectively delivers desirable sounds that are audible at volume levels that are healthy to the fetus, yet inaudible to persons near the expectant mother.

There is a need for a fetal sound system which can allow the fetus to be exposed to high-quality reproduction of sounds of voices of family not in geographic proximity to the pregnant woman. For instance, there is a need for a fetal sound system which can deliver in high fidelity the voice of a father who is away on military service.

There is also a need for an apparatus that transmits sound to the fetus with higher fidelity, so that the sound heard by the fetus is a closer representation of what would be heard after birth, so that later the baby is better able to recognize the voices and music that had been transmitted prenatally. Moreover, there is a need for the ability to more precisely control the acoustic volume delivered to the fetus, so as to maintain healthy sound levels and have the most beneficial results.

Additionally, there is a need for lighter weight devices that are not cumbersome or tiring for the mother to wear. There is also a need for devices with a longer battery life, in order to reduce the hassle and costs associated with purchasing and changing batteries.

SUMMARY OF THE INVENTION

The present invention provides innovations over the prior art allowing greater comfort for the expectant mother, greater sound fidelity delivered to the fetus, and greater battery life. In one aspect, the present invention provides a small, durable convex sound transducer which inherently provides excellent acoustic contact with the expectant mother's abdomen without the inconvenience and possible skin irritation of a gel at the transducer/skin interface. In another aspect, the present invention provides for custom-shaping the frequency spectrum of the sound transmitted to the fetus, depending on the physiological characteristics of the expectant mother, and how far into the term of pregnancy the expectant mother is. In a preferred embodiment, the spectral pre-shaping applied to sounds broadcast to the fetus is varied automatically throughout the term of pregnancy to compensate for spectral shaping variations which occur due (for instance) to the change in the thickness of the lining of the uterus throughout the term of pregnancy.

In a preferred embodiment, digital signal processing techniques are used to shape the frequency spectrum of the signal fed to the transmitting transducer, in order that the desired sound spectrum is received at the ears of the fetus. In addition, a preferred embodiment of the present invention provides a monitoring transducer, and digital signal processing techniques are used to shape the spectrum of the sounds picked up by the monitoring transducer so that the sounds the mother hears at the monitoring transducer (including fetal heartbeat) are close in spectral content to the sounds the fetus hears.

Unlike typical loudspeaker design, where efficiency and fidelity are achieved in part through matching the acoustic impedance of the speaker driver to air, in the case of a fetal sound system, efficiency and fidelity are achieved in part by matching the acoustic impedance of the speaker driver to the acoustic impedance of the tissue of the expectant mother's abdomen. Air has a very low density, so drivers designed to be efficient in air are designed to have a large surface area and are made typically of very light delicate material. Since the density of body tissue is approximately 1000 times the density of air, there is no need to compromise durability of the acoustic driver, since an effectively "low density" driver is not desirable. Indeed, the density of many durable plastics are close enough to the density of body tissue to provide a much better acoustic impedance match to body tissue than even very good loudspeakers are to air.

In loudspeaker design, rigidity is typically achieved by making a conical driving surface where the surface is convex facing outward from the speaker. The convex surface presents no problem in making good contact with the air, because air naturally flows to fill the surface and contact it uniformly. The abdomen of an expectant mother does not flow like air to fill a convex transducer, and thus a typical speaker diaphragm makes very non-uniform contact when placed in contact with a mother's abdomen. For this reason, the best fetal sound systems known in the art have attempted to improve the acoustic contact between the sound transducer and the mother's abdomen by filling in gaps between the transducer and the abdomen with a gel or the like.

Since the expectant mother's abdomen is predominantly convex and naturally elastic, the convex inelastic transducer used in a preferred embodiment of the present invention will inherently make uniform good acoustic contact without the need of gel or the like when pressed into contact with the mother's abdomen, because there are inherently no gaps between the adjacent surfaces which a gel would be needed to fill in. In a preferred embodiment, the convex transducer of the present invention is made from a hypoallergenic, waterproof material. Suitable materials include plastics such as polytetrafluoroethylene, nylon, acrylonitrile butadiene styrene (ABS), or the like.

Fetal sound systems which employ spectral pre-shaping to compensate for the frequency-dependant acoustic attenuation of the expectant mother's abdomen are known in the art, but systems known in the art provide a predetermined spectral pre-shaping, and that pre-shaping will not be optimal for all expectant mothers. Muscle and fatty tissues in humans produce much more attenuation to sound waves, and have a much more frequency-dependent attenuation than does water. For a given transducer position, the path from the sound transducer to the fetus will provide a different amount of attenuation for different women, and for a given woman, the path from the sound transducer to the fetus will provide a different amount of attenuation depending on where the transducer is placed, and how far into the term of pregnancy the expectant mother is. The present invention is able to provide the correct spectral pre-shaping, and the correct volume for any particular expectant mother at any stage of pregnancy. In a preferred embodiment, ultrasound measurements made during the term of pregnancy are used to calibrate the spectral shaping provided by the present invention to maintain optimal sound fidelity and volume at the ears of the fetus. In a preferred embodiment, once the calibration is complete, further spectral shaping variations are calculated automatically based on how far into the term of pregnancy the expectant mother is.

In a preferred embodiment, an acoustic monitoring transducer of the present invention serves to acoustically pick up sounds from the fetus (such as fetal heartbeat), and such sounds are made available to the expectant mother through a standard headphone interface.

Unlike the cumbersome belts of the prior art, the preferred placement geometry for the transducers of the present invention, and the reduced size and weight and increased efficiency of the transducers of the present invention allow the transducers and electronics of the present invention to be worn in a thin, small, flexible package which tucks inside just below the elastic waistband of typical panties, and is supported by that elastic waistband. In an alternate preferred embodiment, the acoustic transducers of the present invention are pressed into contact with the skin of the expectant mother's abdomen by a separate elastic or partially elastic belt.

DETAILED DESCRIPTION OF SOME PREFERRED EMBODIMENTS

Figure 1A:
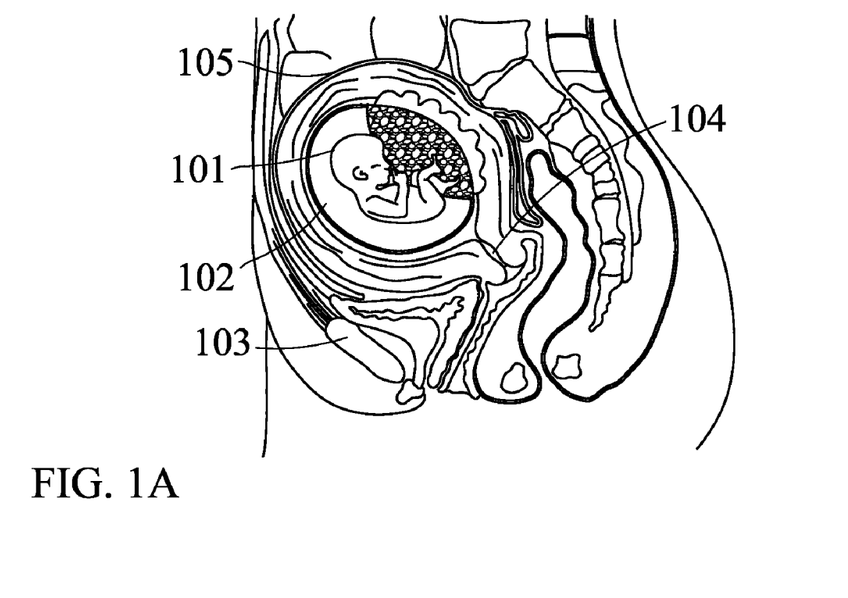
FIG. 1A is a side-view anatomical diagram of an expectant mother and fetus at the $12^{th}$ week of pregnancy.
Figure 1B:
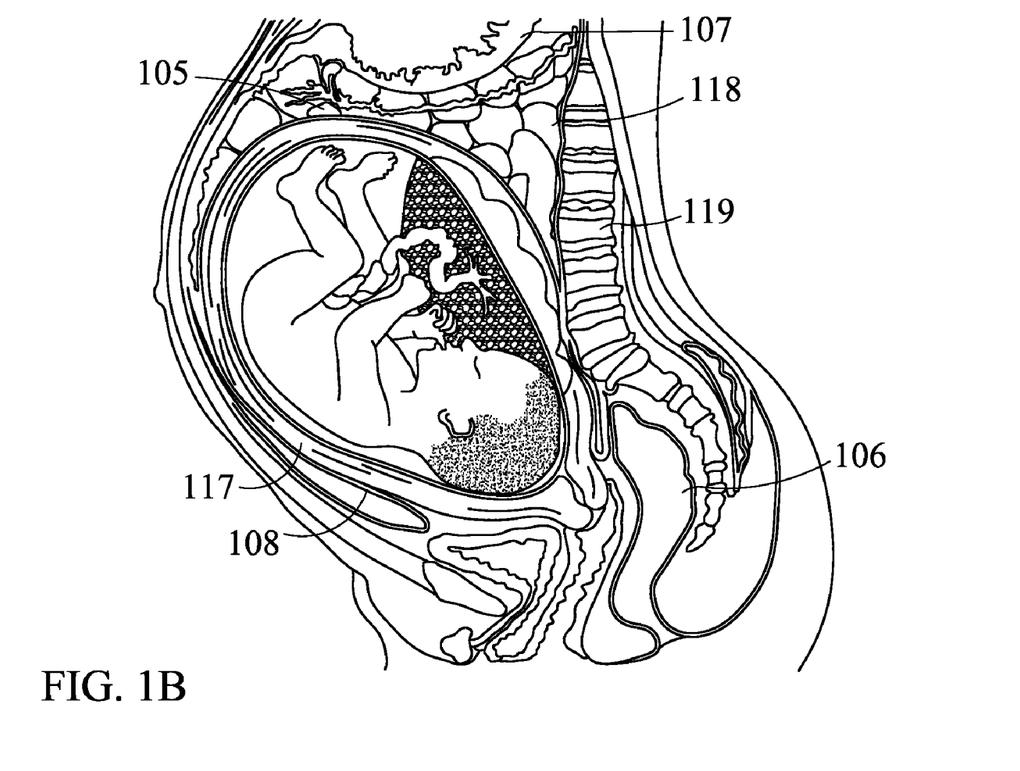
FIG. 1B is a side-view anatomical diagram of an expectant mother and fetus at the $28^{th}$ week of pregnancy.
Figure 1C:
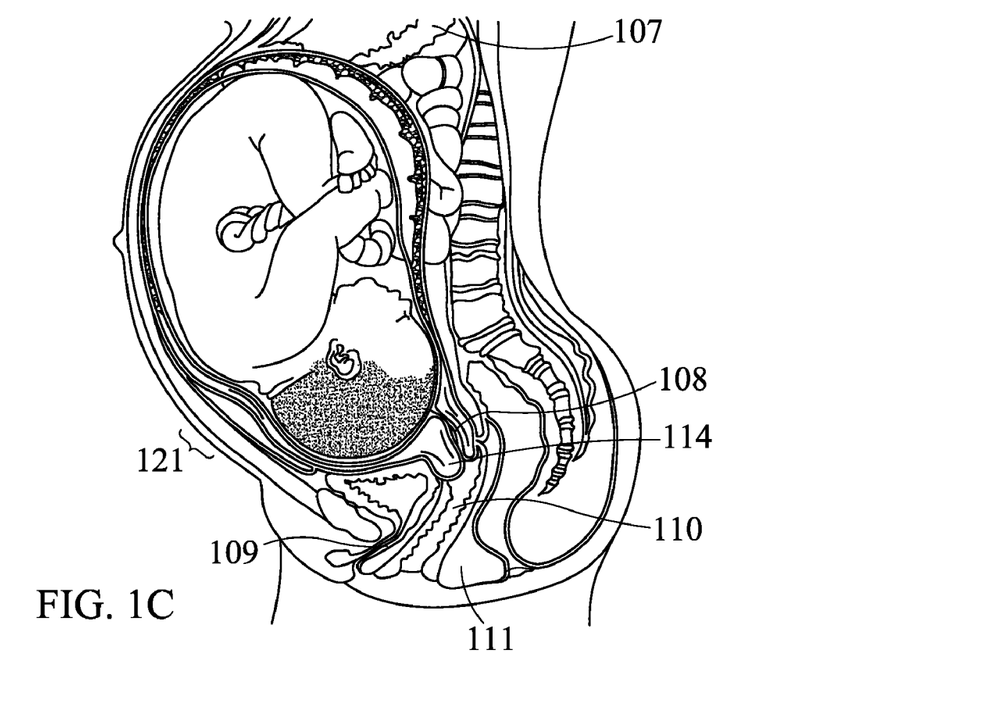
FIG. 1C is a side-view anatomical diagram of an expectant mother and fetus at the $36^{th}$ week of pregnancy.

FIGS. 1A through 1D are anatomical cross-sectional diagrams of an expectant mother and fetus at various stages of the expectant mother's pregnancy. FIG. 1A is typical of the $12^{th}$ week of pregnancy, FIG. 1B is typical of the $28^{th}$ week of pregnancy, FIG. 1C is typical of the $36^{th}$ week of pregnancy, and FIG. 40 is typical of the $40^{th}$ week of pregnancy (considered to be "full term").

Many parts of the mother's anatomy change size, shape and/or position during pregnancy, and the entire fetus changes size, shape, and position during pregnancy. Parts of the mother's anatomy that effectively change size, shape and/or position during pregnancy include the uterus 108, stomach 107, fundus 100 (point on the uterus farthest from the cervix opening), placenta 101, amniotic fluid 102, mucous plug 108, cervix 114, bladder 116, external os 113, internal os 112, descending colon 115, uterine lining 117, and intestines 118.

Parts of the expectant mother's anatomy which may be used as positional reference points during pregnancy include the spine 119, symphysis 103 (fusion between pelvic bones), lower colon 106, perineum 111, umbilicus 120 (belly button), urethra 109, and the opening of the vagina 110.

In order to deliver optimal sound fidelity and the most controllable sound volume to the ears of the fetus, it is desirable that the path the sound waves travel (from the speaker to the ears of the fetus) include as little distance of travel through body tissue is possible, since travel through body tissue results in greater loss at high frequencies and more overall reduction in sound volume than travel through fluids. Sound passing through water (such as amniotic fluid) as opposed to body tissue will remain relatively attenuated, and the frequency spectrum of sound passing through water will remain relatively unaltered compared to the frequency spectrum of sound passing through body tissue. Thus the distance sound travels through water to reach the ears of the fetus is unimportant compared to the distance the sound travels through body tissue. The optimizing criteria for placement of transducers within a preferred embodiment of the present invention is therefore placement of the transducers such that a minimal distance of body tissue must be traversed by sound waves propagating between the transducers of the present invention and the ears of the fetus.

Since medical research shows that the earliest time the fetus can effectively hear sounds is about the 20th week of pregnancy, the anatomy of a typical expectant mother at the time the present invention may first effectively be brought into use is somewhere between the anatomy shown in FIG. 1B and FIG. 1C. A preferred region for placement of transducers of the present invention is therefore the abdominal area roughly halfway between umbilicus 120 (the belly button), and the external opening of the vagina 110.

Figure 2:
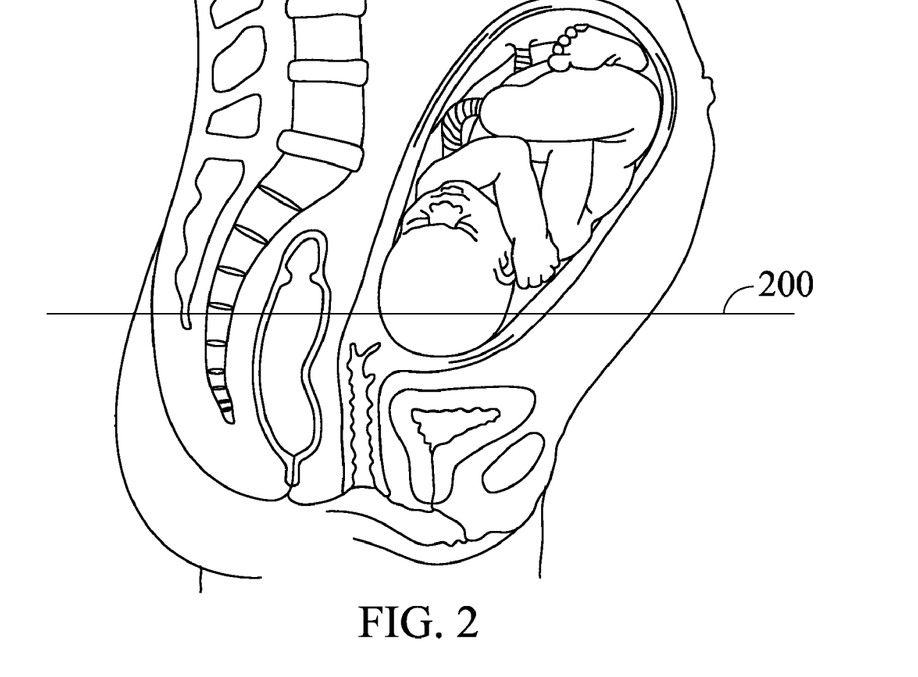
FIG. 2 is a side-view anatomical diagram of a fetus in utero with its head turned to the side.
Figure 3:
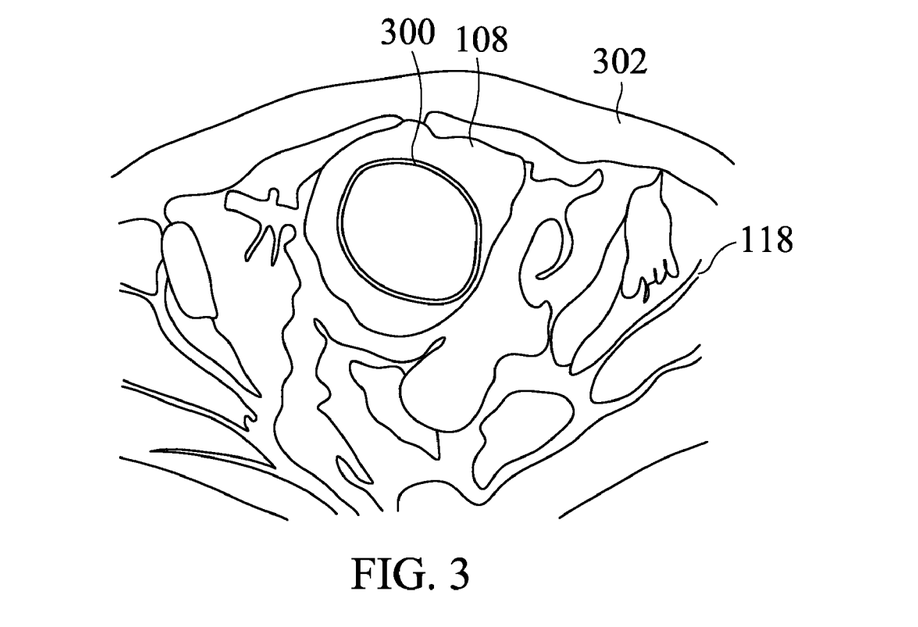
FIG. 3 is a Magnetic Resonance Image (MRI) cross-sectional image through an expectant mother and fetus head, where the cross-section is analogous to cross-sectional line 200 in FIG. 2.

It is normal during pregnancy for the orientation of the head of the fetus to vary from side to side. FIG. 2 depicts a fetus around the 25th week of pregnancy, with its head turned to one side. FIG. 3 is a Magnetic Resonance Image (MRI) cross-sectional image through an expectant mother and fetus head, where the cross-section is analogous to cross-sectional line 200 in FIG. 2. It may be seen in this image how the intestines 118 surround the sides of the uterus 108, and from this it can be seen that by far the least acoustically attenuating path for sound to travel between the transducers of the present invention to the ears of the fetus is achieved when the transducers are placed against the abdomen at a location that is closest to the region between the head and shoulders of the fetus. As can be seen in FIG. 3, this means placing the transducers of the present invention approximately 2 inches to each side of the center line of the front of the expectant mother's abdomen about halfway between the umbilicus 120 (belly button), and the external opening of the vagina 110.

Figure 1D:
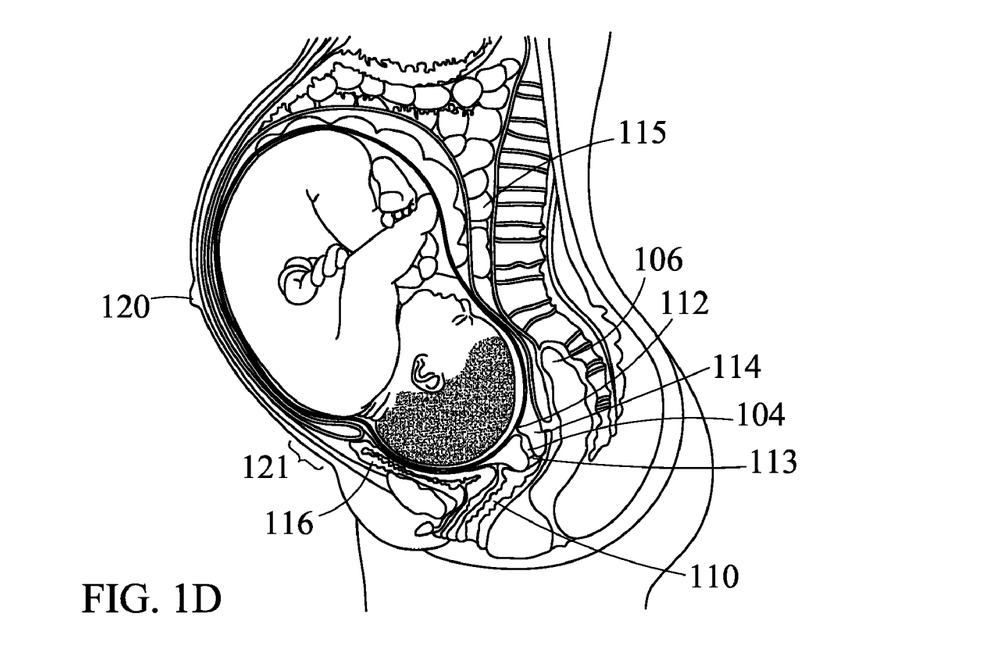
FIG. 1D is a side-view anatomical diagram of an expectant mother and fetus at the $40^{th}$ week of pregnancy.

As can be seen in the progression from FIG. 1B to FIG. 1D, the thickness of the lining of the uterus varies considerably throughout the term pregnancy, becoming thinner as the term of pregnancy progresses. In addition, whatever fat layer exists on the outer portion of the mother's abdomen is also typically stretched thinner as the term of pregnancy progresses. In a preferred embodiment, the firmware of the present invention contains a mathematical model for how the thickness of tissue between the exterior of the mother's abdomen and the fetus varies throughout the term of pregnancy. In a preferred embodiment, calibration information derived from ultrasound measurements may be used at various points during the term of pregnancy to adjust the firmware of the present invention to more accurately represent the actual thickness of tissue between the outer abdominal wall of a particular expectant mother, and the ears of the fetus she is carrying.

Figure 4:
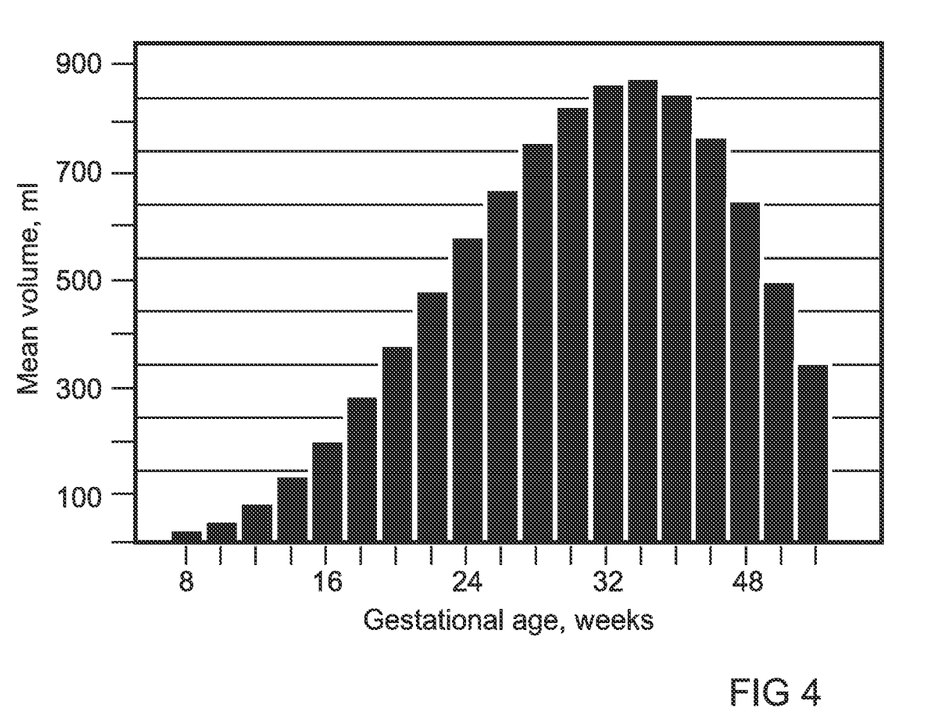
FIG. 4 is a graph depicting typical total amniotic fluid volume versus number of weeks into a typical pregnancy.

As can be seen in FIG. 4, the total volume of amniotic fluid in an expectant mother's uterus varies considerably throughout pregnancy. The amniotic fluid volume increases until roughly the 32nd week of pregnancy, and then decreases for the remainder of the term of pregnancy. During this time the volume of the fetus increases continuously. Transducer placement is most critical during the final four to six weeks of pregnancy, because during this time the amniotic fluid corridor leading from the front of the mothers abdomen to the ears of the fetus is narrowest. In a preferred embodiment, during the later stages of pregnancy, transducer placement may be optimized by actually locating the position of the shoulders of the fetus through ultrasound measurement techniques.

Figure 5:
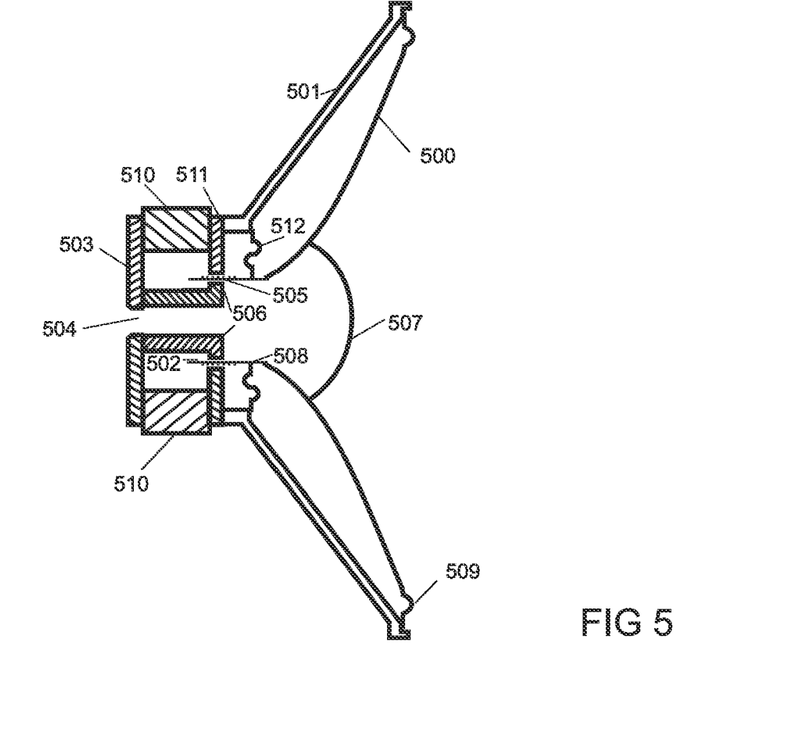
FIG. 5 depicts a cross-section of a typical speaker driver known in the art.

FIG. 5 depicts a cross-section of a typical speaker driver known in the art, and designed for use in air. Magnet 510 forces magnetic field through front plate 511, back plate 503, and center cylinder 506, all of which are made of ferromagnetic material. Magnetic field from magnet 510 is thus guided across air gap 502 through which passes spindle 508 (on which is wound driver coil 505). As current representing sound waves passes through coil 505, coil 505 generates a magnetic field which interacts with the magnetic field generated by magnet 510, producing an axial force on coil 505 which is thus transferred to spindle 508 and in turn to diaphragm 500. The assembly of coil 505, spindle 508, diaphragm 500, and dust cap 507 may be considered to be rigid, and this assembly moves axially in proportion to current pass through coil 505, thus propagating sound waves into the air by moving the volume of air in contact with diaphragm 500 and dust cap 507. Flexible surround 509 and flexible suspension 512 keep the moving assembly centered with respect to the magnet and plate assembly as the moving assembly moves axially.

Figure 6:
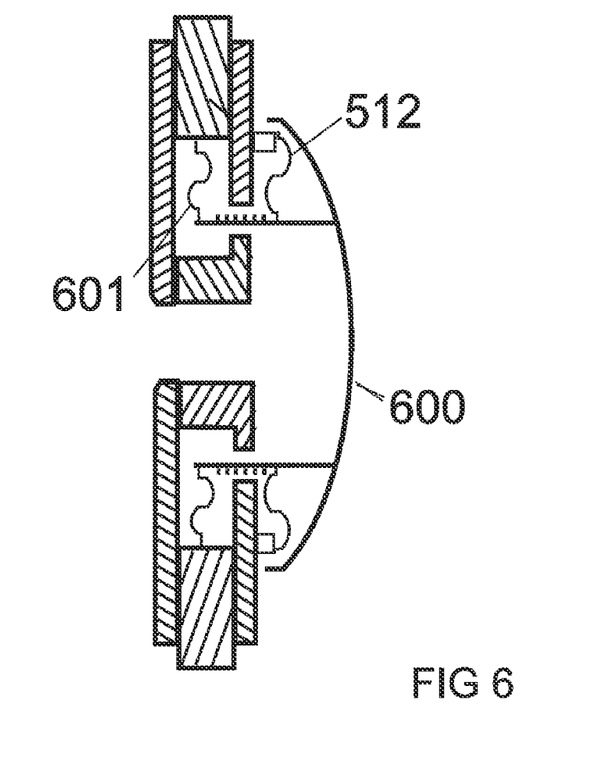
FIG. 6 depicts a cross-section of the specialized speaker driver/microphone of a preferred embodiment of the present invention.
Figure 7:
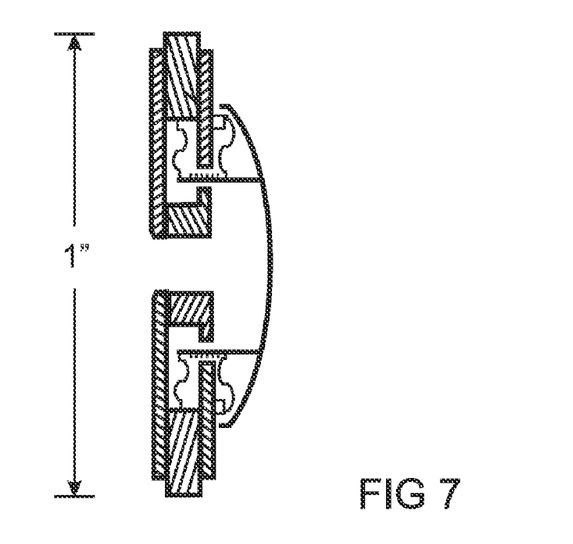
FIG. 7 is a life-size depiction of a cross-section of the specialized speaker driver/microphone of a preferred embodiment of the present invention.

A specialized acoustic driver according to the present invention is depicted in FIG. 6. This driver is analogous to the speaker (known in the art) depicted in FIG. 5, with a few important changes which allow for more efficient transmission of sound into the body, rather than into air. In the transducer designed according to the present invention shown in FIG. 6, speaker frame 501 used in the speaker in FIG. 5 is not needed. Additionally, in place of the driver diaphragm 500 and dust cap assembly 507 shown in FIG. 5, convex rigid diaphragm 600 is substituted. In a preferred embodiment, rigid diaphragm 600 and spindle 508 are created as a single piece, for instance by injection molding techniques. In the driver of the present invention a rear flexible suspension 601 is added behind plate 511 to keep assembly 600 on-axis in the absence of front suspension 509. Because the distance of axial travel required of convex diaphragm 600 is very small compared to the typical excursions which would be required of a speaker diaphragm designed to drive air, the entire magnet and plate assembly of the driver shown in FIG. 6 may be made much thinner than the magnet and plate assembly used for the speaker depicted in FIG. 5. In a preferred embodiment, the actual size of driver (made according to the design of FIG. 6) used in the present invention may be between ¼" in diameter and 1" in diameter, and between ¹⁄₁₆" thick and ¼" thick.

Figure 8:
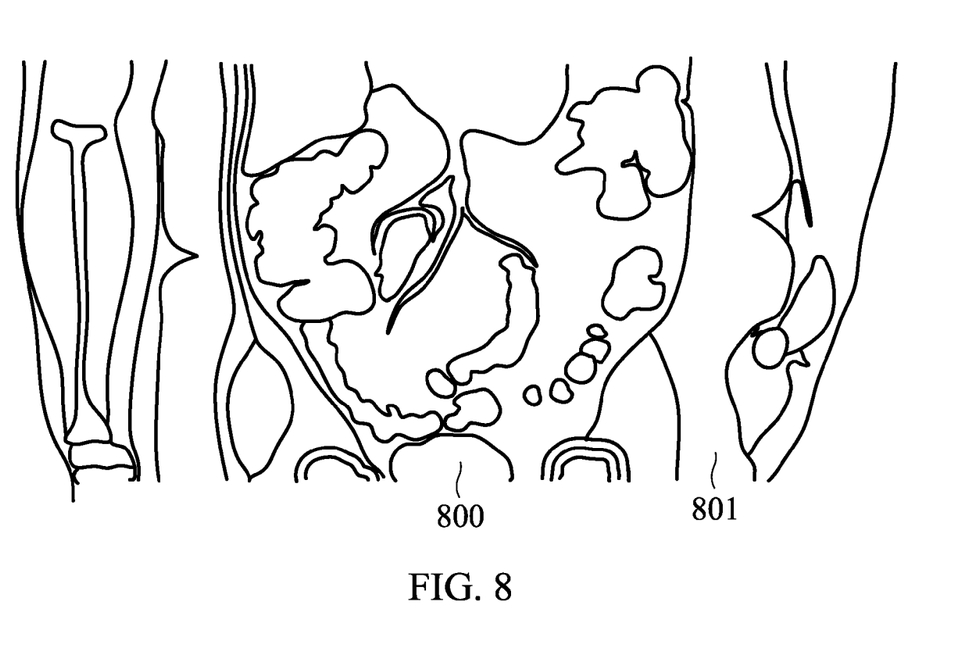
FIG. 8 is a cross-sectional MRI of a 250 pound, 5'6" non-pregnant woman, showing thickness of fat layers.

FIG. 8 is a cross-sectional MRI of a 250 pound, 5'6" non-pregnant woman, showing thickness of fat layers 801, and the size of uterus 800. It can thus be seen that the thickness of attenuative tissue through which sound from the present invention must pass to reach the ears of the fetus may vary substantially depending on the body fat content of the expectant mother. In a preferred embodiment, the abdominal body fat thickness of a particular expectant mother may either be estimated through height and weight measurement, or measured directly through the use of ultrasound, or instrument such as a body fat caliper used in the fitness industry.

Figure 9:
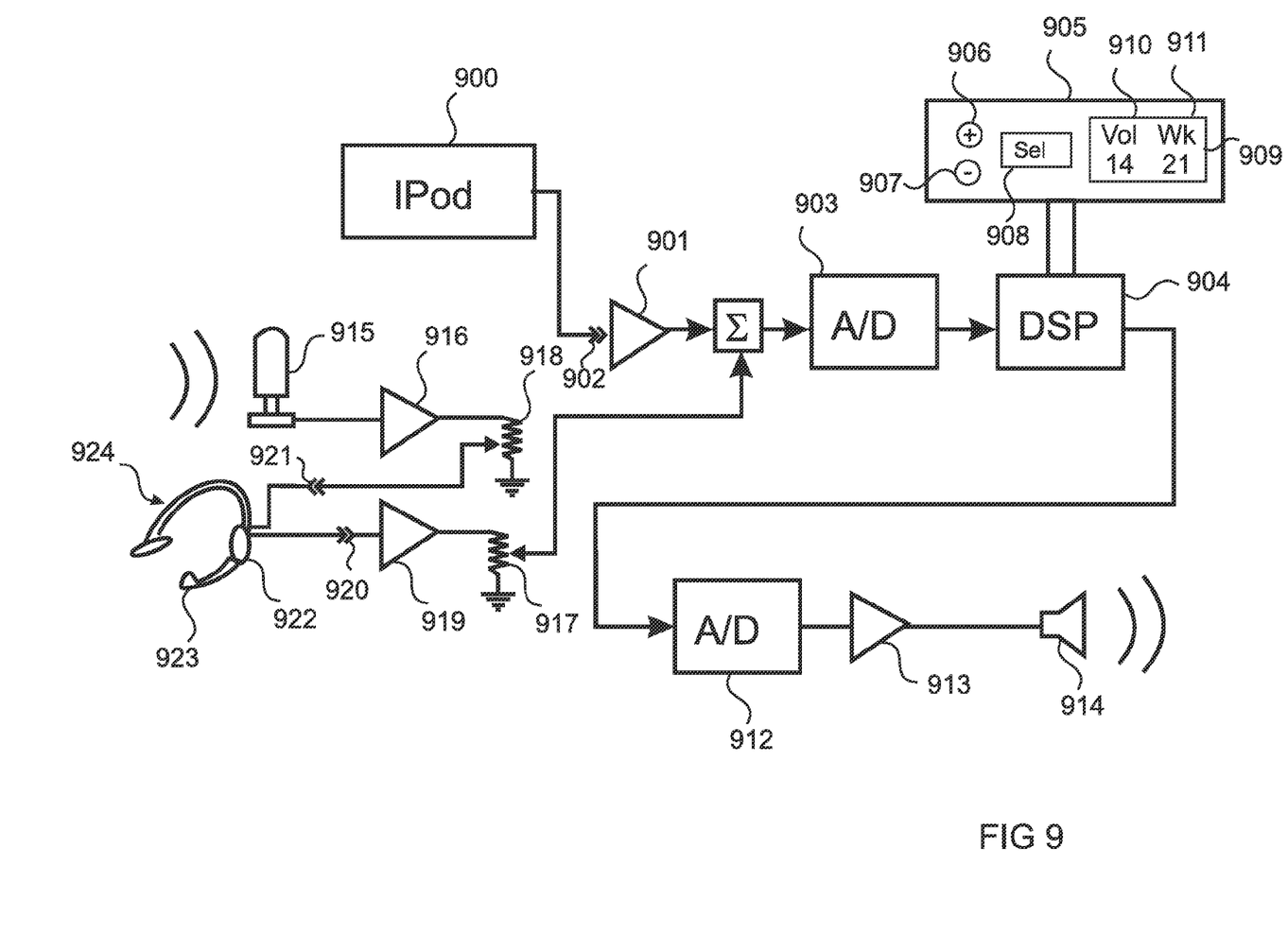
FIG. 9 is an electronic block diagram of a preferred embodiment of the present invention.

FIG. 9 is an electronic block diagram of a preferred embodiment of the present invention. In this preferred embodiment music, voice recordings, and the like reside on recorded audio device 900, which may be an ipod or other MP3 player or a Walkman or radio receiver or the like. In a preferred embodiment, recorded audio device 900 connects to the present invention through audio jack 902. In an alternate embodiment recorded audio device 900 is incorporated within the present invention, and an external connector such as a USB connector is provided for loading digital audio into recorded audio device 900. Buffer amplifier 901 provides a known output impedance to facilitate predictable summation of the outputs of amplifiers 901 and 919. Optional external microphone 923 and optional external earphone 922 are connected to the present invention through audio jacks 920 and 921, respectively. In a preferred embodiment, optional external microphone 923 and optional external earphone 922 are incorporated within headset 924.

Signals from fetal microphone 915 are amplified by amplifier 916, the output volume of which may be controlled through potentiometer 918. Sounds picked up by abdominal and mounted fetal microphone 950 may be listened to by an expectant mother wearing headset 924. If the expectant mother wishes to have the sound of her voice conducted to the fetus she is carrying, she may speak into microphone 923. The signal from microphone 923 is amplified by amplifier 919 and, after being volume regulated by potentiometer 917, amplified signals from microphone 923 are summed with recorded audio signals from recorded audio device 900, and the summed analog audio signals are converted to digital form by A/D converter 903. Digital audio from A/D converter 903 is fed to digital signal processing chip 904, which, in a preferred embodiment has been programmed with firmware to provide spectral shaping and volume adjustment to its incoming digital audio stream which results in an outgoing digital audio stream to D/A converter 912, such that when the analog output of D/A converter 912 is passed through output amplifier 913, which is connected to audio output transducer 914, the audio signal received at the ears of the fetus will be at the desired volume level, and will have spectral characteristics closely approximating those of the analog audio signal at the input to A/D converter 903.

In a preferred embodiment, control panel 905 includes display 909, comprising display segments 910 (which display audio output volume), and display segments 911 (which indicate in which week of pregnancy the expectant mother is). Control panel 905 may also incorporate a display driver, depending on the display driving capabilities of DSP chip 904. Selection button 908, increment button 906, and decrement button 907 provide means for adjusting output volume and week of pregnancy. In a preferred embodiment, DSP chip 904 is provided with a USB interface which may conveniently be connected to a personal computer, and personal computer software is provided for loading calibration parameters for DSP chip 904. In a preferred embodiment calibration parameters which may be loaded include abdominal wall thickness measurements obtained through ultrasound techniques, and fat layer thickness measurements derived either through the mother's height and weight, or through direct measurement techniques such as the use of a fitness fat caliper. In a preferred embodiment, microphone 915 is made from a convex-diaphragm transducer identical to the transducer used for speaker 914.

In an alternate preferred embodiment, control panel 909 may be wirelessly connected to DSP chip 904 (for instance, through a Bluetooth® interface or the like. Such an embodiment allows much of the apparatus of the present invention to be worn under clothing, while the user interface may be conveniently worn outside clothing, for instance as a watch, or in a pocket, or as a clipped device such as a cell phone. In such a preferred embodiment, headset 924 may likewise be a wireless headset, connected through appropriate wireless interface circuitry such as a Bluetooth interface or the like.

In a preferred embodiment, real-time clock 925 runs continuously during the term of pregnancy, and feeds DSP 904, so that DSP 904 can automatically vary spectral shaping appropriately throughout the term of pregnancy.

Figure 11:
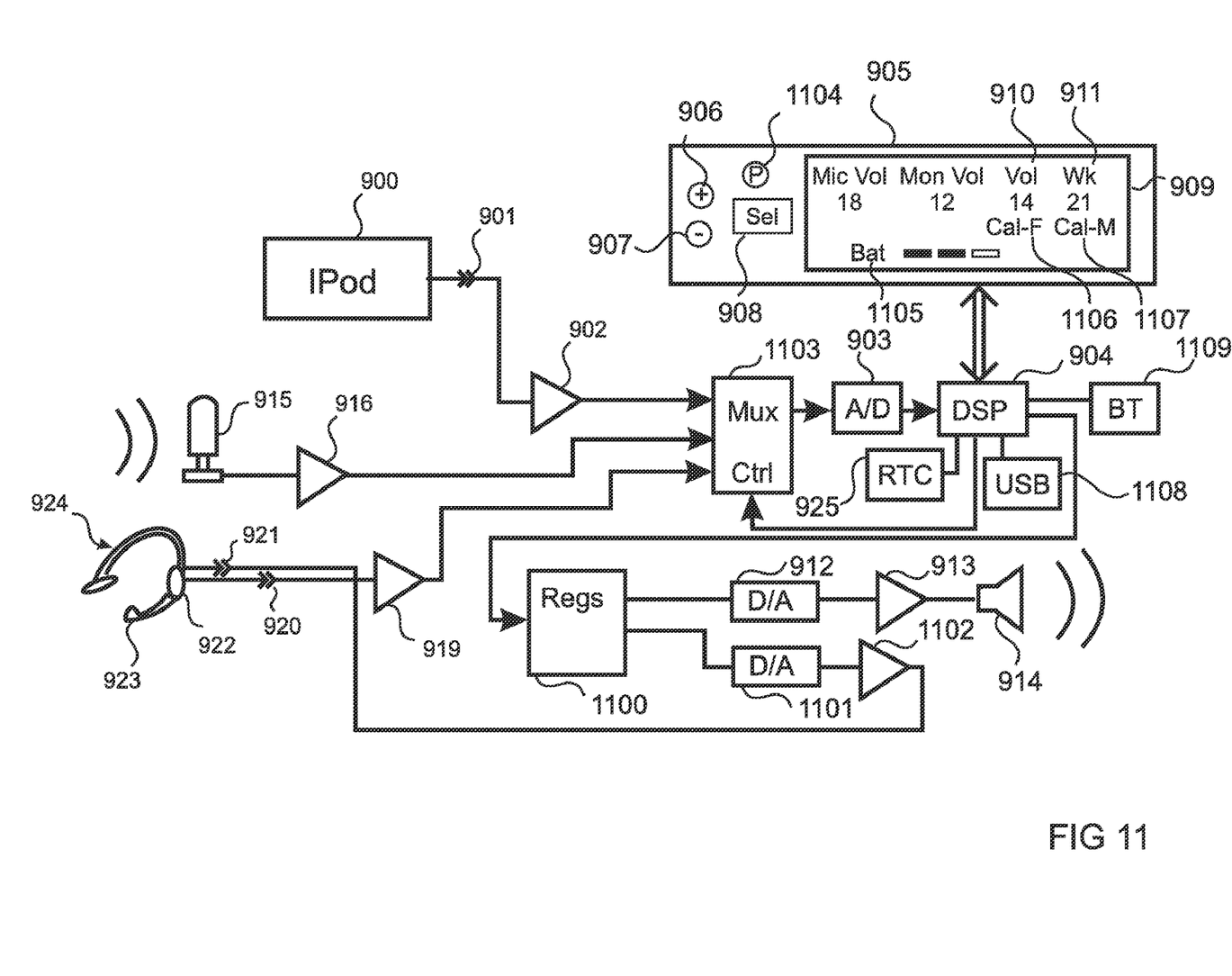
FIG. 11 is an electronic block diagram of a preferred embodiment of the present invention which performs spectral shaping to audio delivered both to the fetus and to an earphone for the expectant mother.

In an alternate preferred embodiment shown in FIG. 11, A/D converter 903 and D/A converter 912 may each be made effectively multi-channel by addition of analog multiplexer 1103 and registers 1100, and DSP chip 904 may additionally be used to spectrally shape the frequency spectrum of the audio signal output through jack 921, such that the sound the sound produced by earphone 922 is a more realistic representation of the sound heard in utero by the fetus. In a preferred embodiment, the frequency spectral shaping applied by DSP 904 to sound picked up by abdominal microphone 915 to create the audio signal presented to earphone 922 is the same frequency spectral shaping applied to audio signals from recorded sound source 900 or microphone 923 to create the audio signal fed to abdominal speaker 914, because the frequency-dependant attenuation being compensated for in each direction (fetus to abdominal transducer, and abdominal transducer to fetus) is approximately the same.

In the preferred embodiment shown in FIG. 11, summing of audio signals from microphone 923 and recorded sound source 900 (which may be an MP3 player, radio, tape player, or the like) is done inside DSP 904, and separate gain controls for audio signals from microphone 922 and recorded audio source 900 are also accomplished in firmware within DSP 904. In the preferred embodiment shown in FIG. 11, digital-to-analog converter 1101 converts successive digital audio samples stored in the earphone register of registers 1100 to an analog audio signal which is buffered by buffer amplifier 1102, which drives earphone 922.

In the preferred embodiment shown in FIG. 11, control panel 905 includes power on/off button 1104, battery strength display 1105, fat layer thickness calibration display 1106, and muscle layer thickness calibration display 1107. In a preferred embodiment, untrasound measurements made on the abdomen of the expectant mother are used to derive the thickness of the fat layer of the mother's abdomen, and the muscle layer thickness of the mother's abdomen, in some embodiments, the uterine lining thickness is measured and a calibration input is provided for uterine lining thickness as well. In a preferred embodiment, calibration factors regarding uterine lining thickness, abdominal muscle thickness, abdominal fat layer thickness, and term of pregnancy (estimated time since conception) are entered through an interface on a personal computer, and calibration factors for the firmware used in DSP 904 are calculated by software running on the personal computer and downloaded to DSP 904 through universal serial bus (USB) interface 1108. In a preferred embodiment, the batteries of the present invention are rechargeable, and external recharging connections are provided so that the unit may be recharged periodically, eliminating possible loss of calibration data and the like if batteries are changed. In a preferred embodiment, calibration data and pregnancy term data are maintained in non-volatile memory such as flash memory, so that data is not lost due to power loss when batteries are changed. In addition, in a preferred embodiment, battery power to real-time-clock 925 is provided by a separate coin-cell battery (such as a watch battery), so that pregnancy term change can still be correctly calculated even if the unit is left unused with dead batteries for some weeks during pregnancy.

Figure 12:
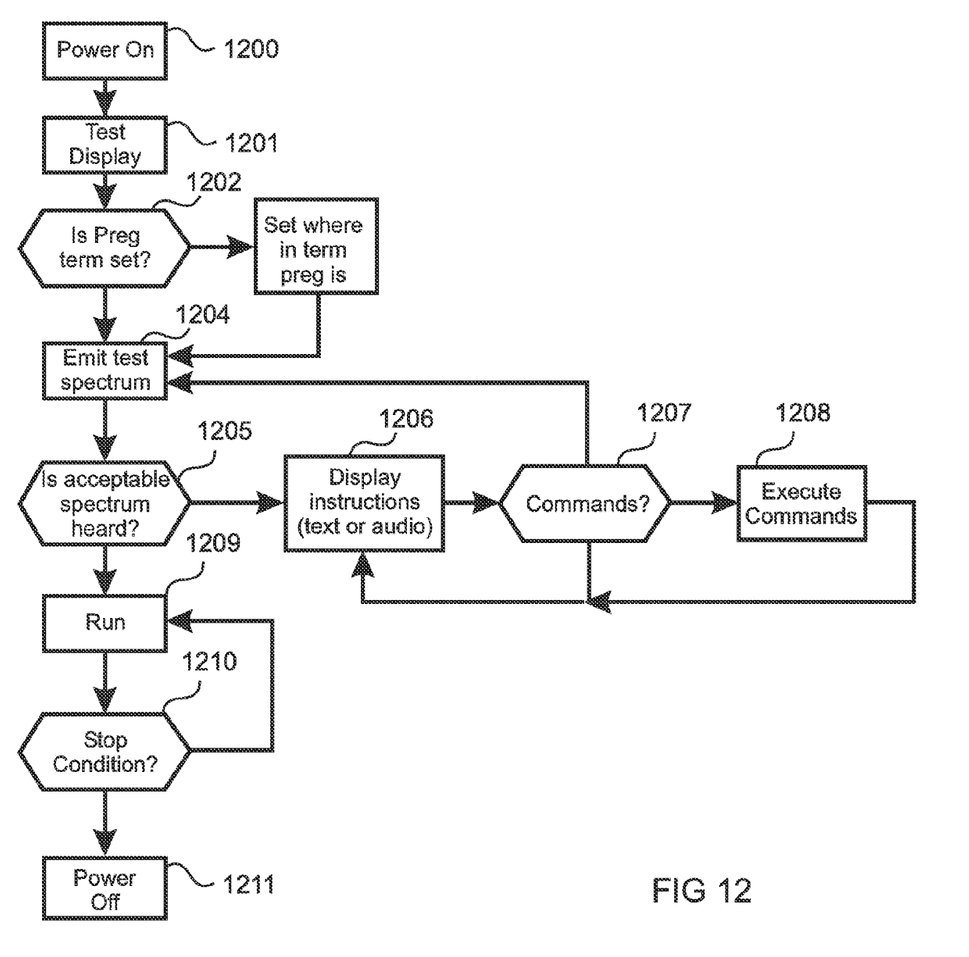
FIG. 12 is a flow chart outlining overall operations of firmware in a preferred embodiment of the present invention.

FIG. 12 is a flow chart outlining overall operations of the firmware of a preferred embodiment of the present invention. When power-on button 1104 is pressed, DSP 904 begins executing firmware instructions in step 1200. System self-test instructions including display test instructions turning on all segments of display 909 are executed in step 1201. In step 1202, memory registers designated to contain pregnancy term information and calibration information are tested. If at lease the pregnancy term register has been previously loaded, execution proceeds to step 1204, where a test sound spectrum is emitted through abdominal speaker 914. If pregnancy term has not been set, then in a preferred embodiment, in step 1203, the user is prompted by both audio prompts delivered through earphone 922 and by text prompts on display 909, asking the user to enter pregnancy term data using the select button 908 and set buttons 906 and 907. In a preferred embodiment, the user may also elect to enter pregnancy term data (and possibly calibration data) through a PC interface and download such data to DSP 904 through USB interface 1108 or wireless interface 1109 (which may be a Blue Tooth interface or the like).

Once pregnancy term data (and optionally calibration data) have been entered, execution proceeds to step 1204, where a test spectrum of sound is emitted from abdominal speaker 914, and the spectrum of sound picked up from abdominal microphone 915 is spectrally analyzed. If the spectral analysis of the sound picked up from abdominal microphone 915 shows an attenuated spectrum which correlates with the spectrum transmitted through abdominal speaker 914, it is assumed that both abdominal speaker 914 and abdominal microphone 915 are in proper contact with the abdomen of the expectant mother, and execution proceeds to step 1209. If the spectrum of sound picked up at abdominal microphone 915 is out of the allowable tolerance range, then execution proceeds to step 1206.

In step 1206, the assumption is made that the unit is not in contact with the expectant mother's abdomen, and it is therefore assumed that the user should be instructed to either put the unit in contact with the mother's abdomen, or enter calibration data or the like. In a preferred embodiment, instructions for such operations are provided both in text (on display 909), and in audio (through earphone 922). If commands are given or calibration data is entered in step 1206, execution proceeds to step 1207, where commands are analyzed. If it is found in step 1207 that a "run" command has been entered (done in a preferred embodiment by briefly pressing power button 1104, then execution re-enters step 1204 and a test spectrum is emitted from speaker 914. If it is found in step 1207 that a command other than "run" has been entered, then the commands entered are executed in step 1208 and execution returns to "command-ready" step 1206.

Once step 1209 has been entered, sound signals from recorded sound source 900 and user microphone 915 are broadcast through abdominal speaker 914 after being appropriately spectrally shaped by DSP 904. Periodically, step 1210 is entered, to check whether the user has pressed power button 1104, to power down the unit. If it is found that the power button has been pressed, the present invention enters a low-power "off" state in step 1211.

Figure 13:
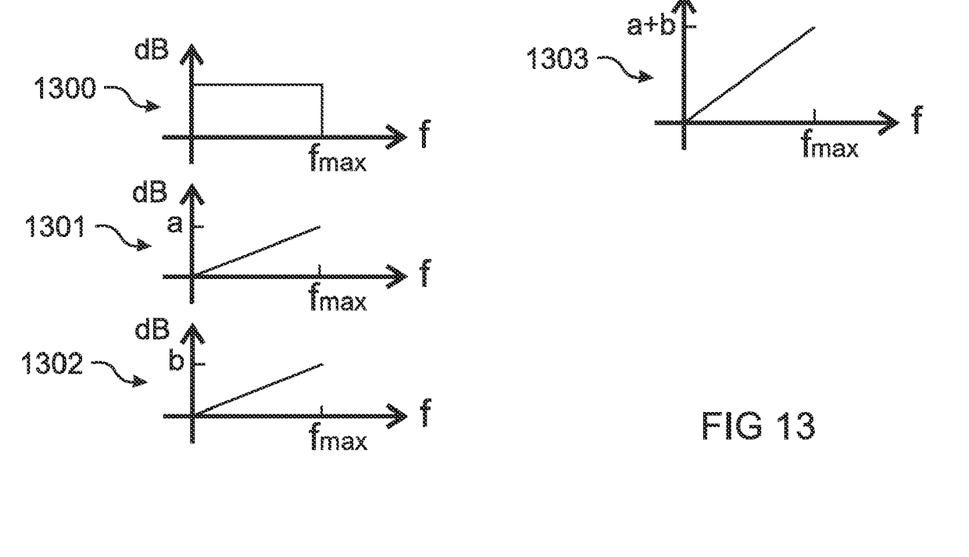
FIG. 13 shows spectral characteristics of a test signal, and spectral attenuation characteristics of a muscle layer, a fat layer, and a combined muscle and fat layer.

In FIG. 13, spectrum 1300 represents a white noise frequency spectrum as might be used as a test spectrum in the present invention. Spectrum 1301 represents the frequency-dependant attenuation that might be caused by sound passing through the muscle layer of an expectant mother's abdomen. Spectrum 1302 represents the frequency-dependant attenuation that might be caused by sound passing through the fat layer of an expectant mother's abdomen. Spectrum 1303 represents the frequency-dependant attenuation that might be caused by sound passing through the combined muscle, fat, and uterine lining layers of an expectant mother's abdomen. In the frequency domain, multiplying spectrum 1300 by a gain spectrum equivalent to attenuation spectrum 1303 and broadcasting that multiplied spectrum through speaker 914 will result in spectrum 1300 being received at the ears of the fetus.

Figure 14:
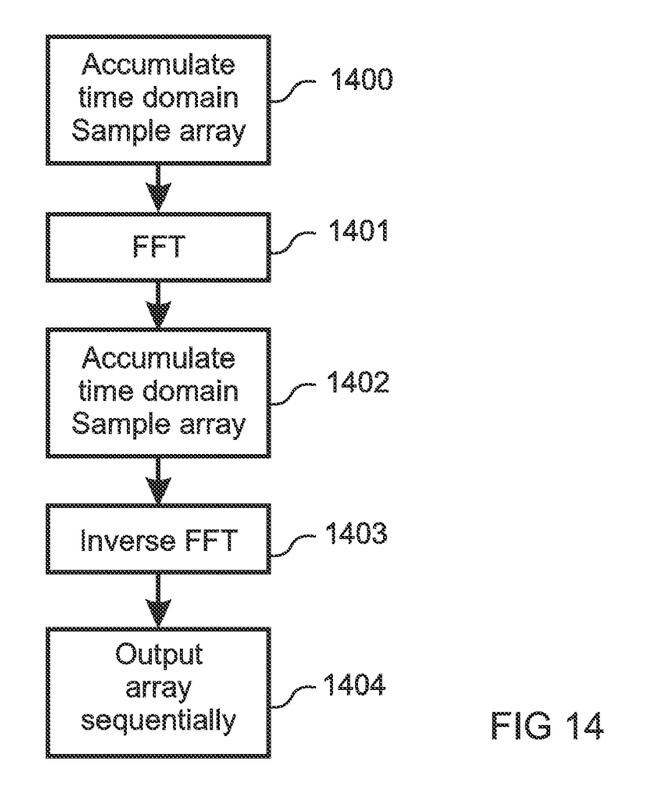
FIG. 14 is a high-level flow chart for the frequency spectral shaping function performed by the firmware in a preferred embodiment of the present invention.

FIG. 14 is a high-level flow chart for the frequency spectral shaping function performed by the firmware in a preferred embodiment of the present invention. In step 1400, an array of sequential time domain samples of audio from recorded audio source 900 and/or user microphone 923 are gathered and stored. In step 1401, a fast Fourier transform (FFT) of this time domain array is calculated. In step 1402, the FFT of the input sound sample set is multiplied by attenuation spectrum 1303, producing an FFT product array. In step 1403, the inverse FFT of the FFT product array is calculated, producing an array of time-domain output digital audio samples. In step 1404, the output audio samples from the calculated time-domain output sample array are sequentially converted to analog and the resultant time-domain analog audio signal is fed to abdominal speaker 914. In a preferred embodiment, an identical spectral shaping process is used to convert audio sensed through abdominal microphone 915 into audio fed to earphone 922, so that the mother can hear sounds such as the fetal heartbeat in an un-muffled way, similar to how the fetus would hear such sounds.

Figure 10:
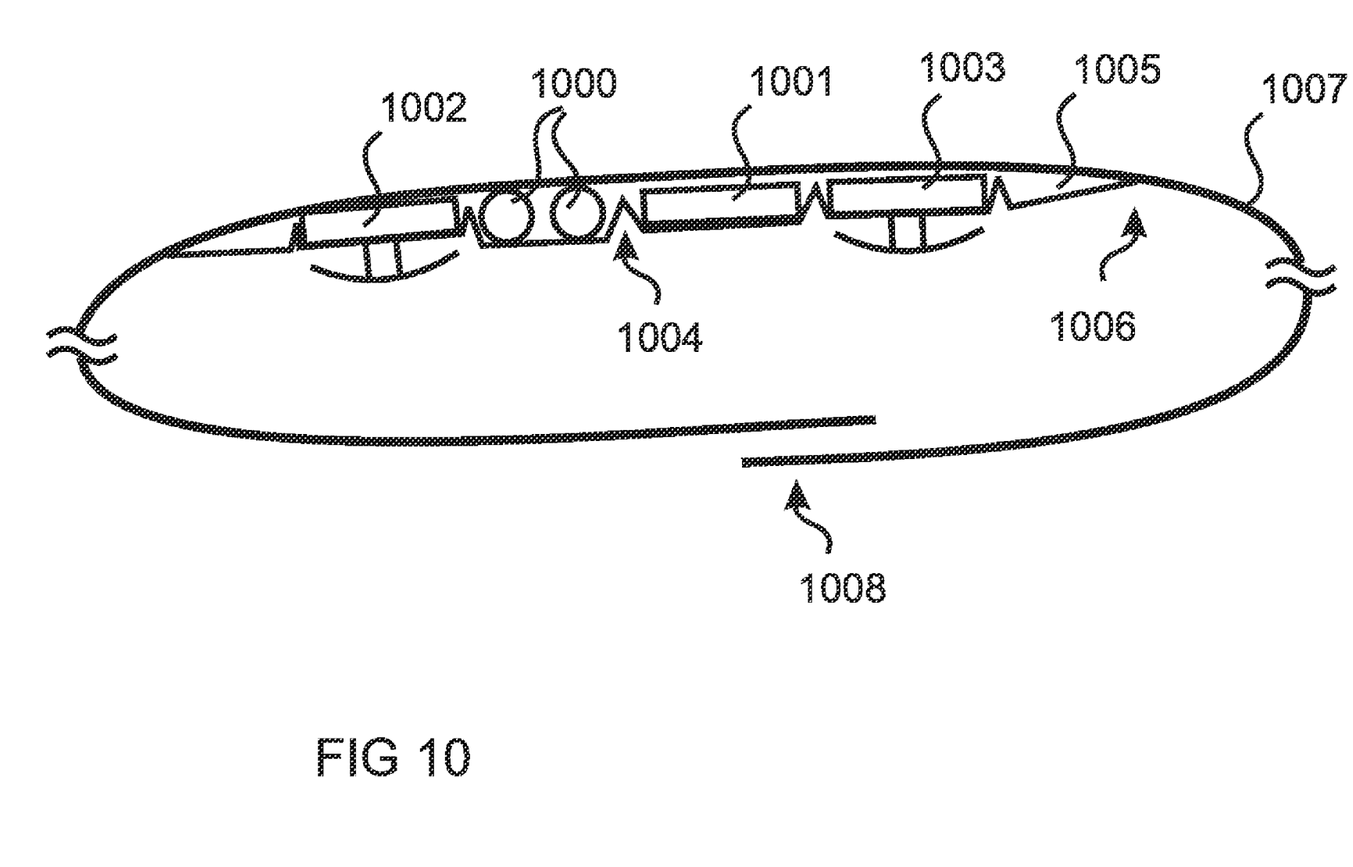
FIG. 10 is a mechanical cross-sectional drawing of a belt according to the present invention.

FIG. 10 is a mechanical cross-sectional drawing of a belt according to the present invention. In a preferred embodiment, microphone transducer 102 and speaker transducer 103 are convex-diaphragm transducer's of design similar to FIG. 6. Batteries 1000 supply power to electronics module 1001 which contains much of the circuitry of FIG. 9. Elastomeric housing 1005 is made additionally flexible by V-notches 1004. In a preferred embodiment, Delta 1007 is integral with elastomeric housing 1005, smoothly joining elastomeric housing 1005 at tapered ends 1006. In a preferred embodiment all or part of belt 1007 is formed of elastic material, and belt coupling mechanism 1008 may be a hook and loop coupling mechanism (such as typically used on bra straps), a hook and loop fastener such as Velcro®, or the like.

What is claimed is:

1. A fetal sound system comprising:
    an audio input that is able to receive one or more analog audio input signals to be transmitted to the ears of an expectant mother's fetus;
    an analog to digital converter having an input coupled to the audio input, said analog to digital converter for converting each of the received one or more analog audio input signals to a digital audio signal;
    a digital signal processor, having an input coupled to an output of the digital to analog converter, the digital to analog converter able to sum together and spectrally shape each of the one or more digital audio signals to compensate for spectral attenuation that would otherwise occur if the one or more analog input signals were directly transmitted, as received, between the expectant mother's abdominal area and the ears of the fetus;
    a digital to analog converter, coupled to an output of the digital signal processor, the digital to analog converter for converting the summed and spectrally shaped one or more digital audio signals to a summed and spectrally shaped analog audio output signal; and
    a transducer, coupled to the digital to analog converter, the transducer for converting the spectrally shaped analog audio output signal to a summed and spectrally shaped acoustic signal and for transmitting the summed and spectrally shaped acoustic signal to the ears of the fetus when the transducer is coupled to the abdominal area of the expectant mother.

2. The fetal sound system of claim 1, wherein the transducer comprises a convex diaphragm.

3. The fetal sound system of claim 2, wherein the transducer further comprises a spindle formed integrally with the convex diaphragm to form a driver assembly.

4. The fetal sound system of claim 3, wherein the spindle is flexibly supported at both of its ends to axially stabilize the driver assembly.

5. The fetal sound system of claim 1, wherein the one or more digital signals are spectrally shaped in accordance with parametric data representative of physical characteristics of the expectant mother.

6. The fetal sound system of claim 5, wherein the parametric data by which the one or more digital audio signals are spectrally shaped includes data representative of at least one of: the thickness of the fat layer, the thickness of the muscle layer, the thickness of the uterine lining, interposed between the surface of the expectant mother's abdominal area and the fetus.

7. The fetal sound system of claim 6 wherein at least some of the parametric data by which the one or more digital audio signals are spectrally shaped is altered from an initial value as a function of time remaining of the expectant mother's term and statistical data defining average changes in the at least some parametric data for expectant mothers over a typical pregnancy term.

8. The fetal sound system of claim 6 wherein the initial value of at least some of the parametric data by which the digital audio signals are spectrally shaped is derived from ultrasound images of the expectant mother.

9. The fetal sound system of claim 8 wherein at least some of the parametric data by which the digital audio signals are spectrally shaped is periodically updated from ultrasound images taken of the expectant mother over the expectant mother's term.

10. The fetal sound system of claim 1 further comprising:
    a microphone for sensing acoustic signals generated by the fetus of the expectant mother when coupled to the surface of the mother's abdominal area and for converting the sensed acoustic signals into electrical signals;
    a buffer having an input coupled to the microphone for buffering the electrical signals; and
    at least one speaker, coupled to an output of the buffer, the at least one speaker for converting the buffered electrical signals into acoustic signals that can be heard through the at least one speaker.

11. The fetal sound system of claim 10 wherein the microphone comprises a transducer including a convex diaphragm.

12. The fetal sound system of claim 11 wherein the transducer of the microphone further comprises a spindle formed integrally with the convex diaphragm to form a driver assembly.

13. The fetal sound system of claim 10, wherein:
    the output of the buffer is first coupled to the analog input,
    the output of the digital signal processor is coupled to a second digital to analog converter having an output coupled to the at least one speaker, and
    the digital signal processor being further capable of spectrally shaping the acoustic signals detected by the microphone to compensate for spectral attenuation of the detected acoustic signals when transmitted between the fetus and the surface of the expectant mother's abdominal area.

14. The fetal sound system of claim 13, wherein:
    the system is capable of generating a test signal that is transmitted by the transducer coupled to the surface of the mother's abdomen,
    the system verifies that the transducer and microphone are in operable contact with the surface of the expectant mother's abdominal area when the test signal is detected by the microphone, and
    the system notifies a user whenever the test signal is not detected by the microphone, indicating that the transducer and the microphone are not in operable contact with the surface of the expectant mother's abdominal area.

15. The fetal sound system of claim 1 wherein one of the at least one analog signals is generated by a vocal microphone.

16. The fetal sound system of claim 1 wherein one of the at least one analog signals is generated by a source of recorded audio.

17. A method of transmitting audio input signals to the ears of a fetus comprising:
    receiving one or more analog audio input signals to be transmitted to the ears of an expectant mother's fetus;
    converting the received one or more analog signals to digital audio signals;
    spectrally shaping the one or more digital audio signals to compensate for spectral attenuation that would have otherwise occurred to the one or more analog input signals had the one or more analog input signals been directly transmitted between the surface of the expectant mother's abdominal area and the ears of the fetus;

converting the summed and spectrally shaped one or more digital audio signals to a summed and spectrally shaped analog audio output signal;

converting the spectrally shaped analog audio output signal to a summed and spectrally shaped acoustic signal; and transmitting the summed and spectrally shaped acoustic signal to the ears of the fetus through the abdominal area of the expectant mother.

18. The method of claim 17, wherein the one or more digital signals are spectrally shaped in accordance with parametric data representative of physical characteristics of the expectant mother.

19. The method of claim 18, wherein the parametric data by which the one or more digital audio signals are spectrally shaped includes data representative of at least one of: the thickness of the fat layer, the thickness of the muscle layer, the thickness of the uterine lining, interposed between the surface of the expectant mother's abdominal area and the fetus.

20. The method of claim 18 wherein said method further comprises periodically updating at least some of the parametric data from an initial value as a function of time remaining of the expectant mother's term based on statistical data defining average changes in the at least some parametric data for expectant mothers over a typical pregnancy term.

21. The method of claim 17 further comprising:

sensing audio signals emanating from within the expectant mother;

spectrally shaping the sensed signals to compensate for spectral attenuation of the sensed signals that will occur as they travel from their source to the surface of the expectant mother's abdominal area; and providing the spectrally shaped sensed signals to speakers to be heard by a user.

* * * * *